US009169320B2

(12) United States Patent
Miyazaki et al.

(10) Patent No.: US 9,169,320 B2
(45) Date of Patent: Oct. 27, 2015

(54) ANTIBODY TO N-TERMINAL REGION OF HEMOGLOBIN β-CHAIN

(75) Inventors: Osamu Miyazaki, Ryugasaki (JP); Kohei Takubo, Ryugasaki (JP); Syunsuke Kurashita, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 13/139,201

(22) PCT Filed: Dec. 10, 2009

(86) PCT No.: PCT/JP2009/006768

§ 371 (c)(1), (2), (4) Date: Jun. 10, 2011

(87) PCT Pub. No.: WO2010/067611

PCT Pub. Date: Jun. 17, 2010

(65) Prior Publication Data

US 2011/0311989 A1 Dec. 22, 2011

(30) Foreign Application Priority Data

Dec. 11, 2008 (JP) ................................ 2008-316173

(51) Int. Cl.

| | |
|---|---|
| ***C07K 16/18*** | (2006.01) |
| ***C12N 5/20*** | (2006.01) |
| ***G01N 33/531*** | (2006.01) |
| ***G01N 33/72*** | (2006.01) |
| ***C12N 5/16*** | (2006.01) |
| ***C07K 14/805*** | (2006.01) |

(52) U.S. Cl.

CPC ............... *C07K 16/18* (2013.01); *C07K 14/805* (2013.01); *C12N 5/163* (2013.01); *G01N 33/531* (2013.01); *G01N 33/721* (2013.01); *G01N 33/723* (2013.01); *C07K 2317/33* (2013.01); *C07K 2317/34* (2013.01)

(58) Field of Classification Search

CPC ............... C07K 16/44; C07K 2317/34; C07K 2317/33; C12N 5/163; G01N 33/531; G01N 33/577; G01N 33/72; G01N 33/721; G01N 33/723; G01N 2033/53; G01N 2333/46; G01N 2333/805; G01N 2400/02; G01N 2410/00; G01N 2410/244

USPC ............ 435/7.25, 7.5, 7.92, 7.93, 7.94, 7.95, 435/14, 70.21, 329, 331, 343, 973; 436/518, 524, 528, 534, 547, 548, 66, 436/67; 530/387.9, 388.25, 388.7, 389.3, 530/389.6, 391.1, 391.3, 806

See application file for complete search history.

(56) References Cited

U.S. PATENT DOCUMENTS

| | | | | |
|---|---|---|---|---|
| 4,658,022 | A | 4/1987 | Knowles et al. | |
| 5,470,759 | A | 11/1995 | Sugiyama et al. | |
| 6,294,062 | B1 * | 9/2001 | Buck et al. | 204/400 |
| 2002/0090632 | A1 | 7/2002 | Buck, Jr. et al. | |

FOREIGN PATENT DOCUMENTS

| | | |
|---|---|---|
| JP | 61 172064 | 8/1986 |
| JP | 6 66796 | 3/1994 |
| JP | 2004-59477 A | 2/2004 |

OTHER PUBLICATIONS

Jemmerson et al., 1985. Analysis of an evolutionarily conserved antigenic site on mammalian cytochrome c using synthetic peptides. Proc. Natl. Acad. Sci. USA 82: 1508-1512.*

Jeppsson, J. et al., "Approved IFCC Reference Method for the Measurement of $HbA_{1c}$ in Human Blood", Clin. Chem. Lab. Med., vol. 40, pp. 78-89, (2002).

Tominaga, M. et al., "Tonyobyo Kanren Kensa No Hyojunka Ni Kansuru linkai: Kemoglobin Alc Hyojun Busshitsu JDSLot2 No IFCC-chi Ni Tsuite", The Journal of the Japan Diabetic Society, vol. 46, pp. 775-778, (2003) (with English abstract).

International Search Repot and Written Opinion (English translation) Issued Feb. 2, 2010 in PCT/JP09/006768 filed Dec. 10, 2009.

Extended European Search Report issued Jan. 22, 2013, in European Patent Application No. 09831717.5.

U.S. Appl. No. 13/139,239, filed Jun. 10, 2011, Miyazaki, et al.

* cited by examiner

*Primary Examiner* — Gail R Gabel
*Assistant Examiner* — James L Grun
(74) *Attorney, Agent, or Firm* — Oblon, McClelland, Maier & Neustadt, L.L.P.

(57) ABSTRACT

Provided is a general-purpose technique capable of measuring the HbA1c content, which is comparable to the IFCC reference method. An antibody which reacts with a peptide or a protein having an amino acid sequence of VHLTPE (SEQ ID NO: 1) at the N-terminus in which the N-terminal valine is not modified, but does not react with a peptide or a protein in which the N-terminal valine of the relevant polypeptide or protein is modified.

12 Claims, 8 Drawing Sheets

ANTIBODY TO N-TERMINAL REGION OF HEMOGLOBIN β-CHAIN

CROSS-REFERENCE TO RELATED APPLICATIONS

This application is a National Stage of PCT/JP09/006768 filed Dec. 10, 2009 and claims the benefit of JP 2008-316173 filed Dec. 11, 2008.

FIELD OF THE INVENTION

The present invention relates to an antibody that recognizes unmodified N-terminal region of hemoglobin β-chain, and a method for measuring hemoglobin A1c using the antibody.

BACKGROUND OF THE INVENTION

Among glycated hemoglobins in which sugar is bound to hemoglobin (hereinafter, referred to as "Hb") in blood, hemoglobin A1c (hereinafter, referred to as "HbA1c") in which the N-terminal valine residue of the hemoglobin β-chain is glycated with glucose, clinically reflects the average blood glucose level of the past one to two months. Therefore, HbA1c is widely used as a marker appropriate for the diagnosis of diabetes or a progress observation of diabetes.

As the method for measuring HbA1c, HPLC methods and immunological assay methods have been used, but because the measurement objects subtly varies with the type of the HPLC column or among the reagent manufacturers, the standardization of the assay is requested. From such a viewpoint, the working group for HbA1c standardization of the International Federation of Clinical Chemistry and Laboratory Medicine (IFCC) determined a standard assay method (hereinafter, referred to as "IFCC reference method") (Non-Patent Document 1). The method involves digesting a red blood cell lysate with a protease, thereby extracting the N-terminal hexapeptide of the hemoglobin β-chain (VHLTPE) (SEQ ID NO: 1), determining the amounts of the glycated N-terminal hexapeptide (f-VHLTPE) (SEQ ID NO: 11) of the HbA1c β-chain and the unmodified N-terminal hexapeptide (VHLTPE) (SEQ ID NO: 1) of the β-chain of hemoglobin AO (hereinafter, referred to as "HbA0") in the extract, and calculating the HbA1c content (%) by the formula shown below:

$$\text{HbA1c content (\%)}=(\text{Amount of f-VHLTPE (SEQ ID NO: 11)}/(\text{amount of f-VHLTPE (SEQ ID NO: 11)}+\text{amount of VHLTPE (SEQ ID NO: 1)}))\times 100=(\text{Amount of HbA1c}/(\text{amount of HbA1c}+\text{amount of HbA0}))\times 100$$

However, since the method for measuring the glycated hexapeptide content according to this method makes use of HPLC-MS or HPLC-capillary electrophoresis, the method requires expensive apparatuses, and the measurement can be made only in particular facilities. Furthermore, there is a problem that the measurement values obtained by this method are different greatly from the HbA1c values obtained by conventional methods (Non-Patent Document 2).

PRIOR ART DOCUMENT

Non-Patent Documents

Non-Patent Document 1: Clin. Chem. Lab. Med. 2002; 40 (1): 78-89

Non-Patent Document 2: Tonyobyo, 2003; 46(9): 775-778

DISCLOSURE OF INVENTION

Problem to be solved by the Invention

Therefore, the object of the present invention is to provide a general-purpose technique for measuring the HbA1c content (%), which is comparable to the IFCC reference method.

Means for Solving Problem

Thus, the inventors of the present invention conducted an investigation to develop an IFCC reference method that replaces a HPLC-MS method or a HPLC-capillary electrophoresis method, and as a result, the inventors succeeded for the first time in the production of an antibody which reacts specifically with the N-terminal hexapeptide VHLTPE (SEQ ID NO: 1) of the Hb β-chain, but does not react with a peptide in which this hexapeptide is modified. The inventors found that when this antibody and HbA1c antibody are used, HbA1c and HbA0 can be measured accurately and conveniently, and the HbA1c content (%) according to the IFCC reference method can be measured with a convenient immunological technique, thus completed the present invention.

That is, the present invention provides an antibody which reacts with a peptide or a protein having an amino acid sequence of VHLTPE (SEQ ID NO: 1) at the N-terminus, but does not react with a peptide or a protein having an amino acid sequence of VHLTPE (SEQ ID NO: 1) at the N-terminus in which the N-terminal valine is modified.

Another object of the present invention is to provide a method for measuring the HbA1c content in a sample, characterized by measuring the amount of HbA0 in a sample using the aforementioned antibody, measuring the amount of HbA1c in the sample using an anti-HbA1c antibody, and calculating the HbA1c content (%) in the sample by the following formula (1):

$$\text{HbA1c content (\%)}=(\text{Amount of HbA1c}/(\text{amount of HbA1c}+\text{amount of HbA0}))\times 100 \quad (1)$$

Effect of Invention

By using the antibody of the present invention, the amount of HbA0 in a sample can be measured accurately and conveniently. Therefore, the HbA1c content (%) according to the IFCC reference method which is based on the amount of HbA0 and the amount of HbA1c in a sample can be measured conveniently and accurately by using the antibody of the present invention.

BEST MODE(S) FOR CARRYING OUT THE INVENTION

Figure 1:
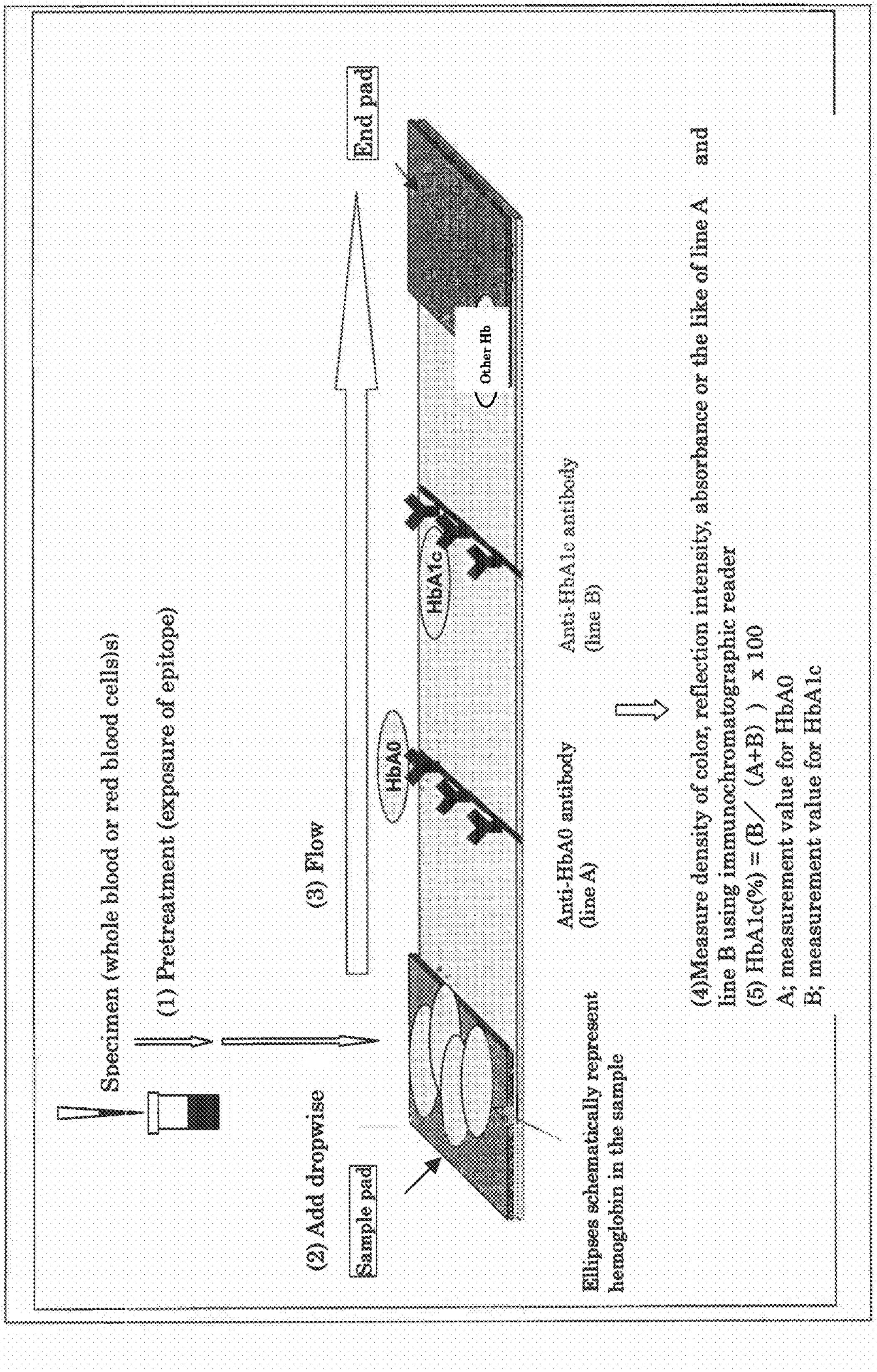
FIG. 1 is a schematic diagram showing the method for measuring HbA1c according to an immunochromatographic method.

The antibody of the present invention is an antibody which reacts with a peptide or a protein having an amino acid sequence of VHLTPE (SEQ ID NO: 1) at the N-terminus in which the N-terminal valine is not modified, but does not react with a peptide or a protein having an amino acid sequence of VHLTPE (SEQ ID NO: 1) at the N-terminus in which the N-terminal valine is modified.

Examples of the peptide having an amino acid sequence of VHLTPE (SEQ ID NO: 1) at the N-terminus in which the N-terminal valine is not modified, include an oligopeptide composed of the amino acid sequence of VHLTPE (SEQ ID NO: 1), and a polypeptide containing the amino acid sequence of VHLTPE (SEQ ID NO: 1). Examples of the protein having an amino acid sequence of VHLTPE (SEQ ID NO: 1) at the N-terminus in which the N-terminal valine is not modified, include hemoglobin A0 having a Hb β-chain, which is a major Hb for normal adults, and hemoglobin A2 (hereinafter, referred to as "HbA2") having a Hb δ-chain in which the N-terminus of the β-chain is not modified. However, HbA2 is a trace component. Therefore, HbA0 is a principal example of the Hb reacting with the antibody of the present invention.

On the other hand, examples of the peptide or protein in which the N-terminal valine is modified, include a peptide or a Hb, which has the amino acid sequence of VHLTPE (SEQ ID NO: 1) at the N-terminus, and in which the N-terminal valine is modified with sugar. HbA1c is an example of the relevant protein.

Therefore, a preferred embodiment of the antibody of the present invention may be an antibody which reacts with a peptide or Hb having the amino acid sequence of VHLTPE (SEQ ID NO: 1) at the N-terminus in which the N-terminal valine is not modified, but does not react with a peptide or Hb having the amino acid sequence of VHLTPE (SEQ ID NO: 1) at the N-terminus in which the N-terminal valine is modified. A more preferred embodiment is an antibody which reacts with HbA0 but does not react with HbA1c.

In addition, the antibody of the present invention is preferably an antibody which does not react with a protein other than Hb, and also does not react with an Hb which does not have the amino acid sequence of VHLTPE (SEQ ID NO: 1), for example, HbF.

The antibody of the present invention may be a polyclonal antibody or a monoclonal antibody, but it is particularly preferable that the antibody be a monoclonal antibody.

Since HbA0 has the sequence VHL (SEQ ID NO: 2) at the N-terminus of the β-chain, the antibody of the present invention can be obtained by a conventional method using a peptide or a protein, which has the amino acid sequence of VHL (SEQ ID NO: 2), as an immunogen. Examples of the immunogen include VHLC (SEQ ID NO: 3), VHLTC (SEQ ID NO: 4), VHLTPC (SEQ ID NO: 5), VHLTPEC (SEQ ID NO: 6), VHL (SEQ ID NO: 2), VHLT (SEQ ID NO: 7), VHLTP (SEQ ID NO: 8), VHLTPE (SEQ ID NO: 1), and antigens in which these peptides are bound to carrier proteins. Examples of the carrier proteins include ovalbumin (hereinafter, referred to as "OVA"), bovine serum albumin (hereinafter, referred to as "BSA"), cationized BSA (hereinafter, referred to as "cBSA"), and keyhole limpet hemocyanin (hereinafter, referred to as KLH). Examples of the method of binding a peptide with a carrier protein include an MBS method (a method of using an m-Maleimidobenzoyl-N-hydroxysuccinimide ester), and an EDC method (a method of using 1-ethyl-3-(3-dimethylaminopropyl)carbodiimide hydrochloride).

The monoclonal antibody of the present invention can be produced according to, for example, a method described in Antibodies, A Laboratory Manual (Cold Spring Harbor Laboratory Press, 1988).

There are no particular limitations on the animal that is used for immunization, and examples of the animal include mouse and rat. The immunization method can be carried out according to a general technique. For example, a suspension of the immunogen with a conventional buffer solution or physiological saline, or a mixture of the immunogen and an auxiliary fluid of a Freund's complete adjuvant or the like, is administered to an animal subcutaneously, intradermally, intraperitoneally or the like so as to provide the primary stimulation, and then the same operation is repeatedly carried out according to necessity. The amount of administration of the antigen is adequately determined in accordance with the route of administration or the type of animal, but the general amount of administration is preferably about 10 μg to 1 mg per administration.

For the immune cells used for cell fusion, spleen cells extracted 3 to 4 days after the final immunization are suitably used. Furthermore, the myeloma cells (hereinafter, referred to as "myeloma cells") that are fused with the immune cells are preferably various known cell strains that have already been established, and examples include NS1 (P3/NSI/I-Ag4-1) [Eur. J. Immunol. 6:511-519 (1976)], SP2/O—Ag14 [Nature 276:269 (1978)], P3-X63-Ag8.653 [J. Immunol. 123:1548 (1979)], and P3-X63-Ag8U.1 [Curr. Top. Microbiol. Immunol. 81:1 (1978)] of mouse; and Y3-Ag1.2.3. [Nature 277: 131-133 (1979)], and YB2/O (YB2/3HL/P2.G11.16Ag.20) [Methods Enzymol. 73B:1 (1981)] of rat.

Cell fusion can be carried out using polyethylene glycol (hereinafter, referred to as "PEG") that is conventionally used, Sendai virus (HVJ), and the like. The technique for cell fusion is similar to the conventional methods, and for example, a solution of a PEG having an average molecular weight of 1000 to 6000 at a concentration of 30% to 60% is added dropwise to a mixed pellet of myeloma cells and immune cells in an amount of about 1 to 10-fold amount of the myeloma cells, to be mixed with the pellet. Selection of the hybridoma is carried out using a conventional selection medium, for example, a medium containing hypoxanthine, aminopterin and thymidine (hereinafter, referred to as "HAT"). Search of a cell strain producing the target antibody and cloning may be carried out by a conventional limiting dilution method, using a hybridoma obtained by culturing in HAT medium.

Cell strains producing the target antibody can be obtained by selecting a hybridoma which produces an antibody that reacts with a peptide or a protein having the sequence of VHLTPE (SEQ ID NO: 1) but does not react with a peptide or a protein in which the N-terminal valine of the relevant peptide or protein is modified, for example, using an ELISA method or a RIA method.

Specifically, first, a monoclonal antibody in the culture supernatant is allowed to react with an immobilized purified HbA0 antigen, and then is allowed to react with a labeled anti-IgG antibody. A hybridoma which produces a monoclonal antibody having high reactivity to HbA0 is screened by an antigen-immobilized ELISA method. The culture supernatant of the hybridoma thus obtained is further subjected to a competitive ELISA method with the peptide VHLTPE (SEQ ID NO: 1) or glycated VHLTPE (f-VHLTPE) (SEQ ID NO: 11), using a plate on which a purified HbA0 antigen is immobilized, and a hybridoma which produces a monoclonal antibody that reacts with the peptide VHLTPE (SEQ ID NO: 1) but does not react with the peptide f-VHLTPE (SEQ ID NO: 11), is selected.

The monoclonal antibody can be produced by a method of culturing the hybridoma according to a conventional method and separating the antibody from the culture supernatant; or a method of administering the hybridoma to a mammal that is compatible with the hybridoma, and collecting the antibody in the ascites fluid.

The monoclonal antibody of the present invention, obtained in this way, reacts with a peptide or a protein in which the N-terminus of the Hb β-chain is not modified but does not react with a peptide or a protein in which the N-terminus of the Hb β-chain is modified. Therefore, the monoclonal antibody is an antibody which reacts with HbA0 but does not react with HbA1c. Accordingly, the monoclonal antibody is useful as an antibody for performing an immunoassay that distinguishes HbA0 from HbA1c.

By using the antibody of the present invention, an assay of HbA1c that is comparable with the IFCC reference method can be carried out. That is, when the amount of HbA0 in a sample is measured by using the antibody of the present invention, the amount of HbA1c in the sample is measured by using an anti-HbA1c antibody, and the HbA1c content (%) in the sample is calculated by the following formula (1):

$$\text{HbA1c content (\%)}=(\text{Amount of HbA1c}/(\text{amount of HbA1c}+\text{amount of HbA0}))\times 100 \quad (1)$$

the HbA1c content in the sample can be measured.

Furthermore, considering the recognition site of the monoclonal antibody of the present invention, the aforementioned formula (1) can also be represented by the following formula (2):

$$\text{HbA1c content (\%)}=(\text{Amount of f-VHLTPE (SEQ ID NO: 11)}/(\text{amount of f-VHLTPE (SEQ ID NO: 11)}+\text{amount of VHLTPE (SEQ ID NO: 1)}))\times 100 \quad (2)$$

The method for measuring HbA0 and the method for measuring HbA1c of the present invention can be performed by any conventional immunological assay method. Here, examples of the immunological assay method include a sandwich ELISA method, a competitive ELISA method, an immunochromatographic method, a latex agglutination method, and a competitive latex agglutination method.

HbA0 and HbA1c can be respectively measured by applying the monoclonal antibody of the present invention to any of the conventional immunological assay methods.

For example, in the case of performing an assay by a sandwich ELISA method, HbA0 or HbA1c can be measured by the following method, using purified HbA0 or HbA1c as a standard substance. That is, a diluted specimen sample is added to an ELISA plate on which the monoclonal antibody of the present invention or an anti-HbA1c antibody is immobilized, to allow the sample to react. Subsequently, an enzyme-labeled anti-hemoglobin antibody (hereinafter, referred to as "anti-Hb antibody") is allowed to react with the sample, and from the changes in the absorbance after color development, HbA0 or HbA1c in the sample can be specifically measured.

In the case of performing an assay by a latex agglutination method, HbA0 or HbA1c can be measured by the following method, using purified HbA0 or HbA1c as a standard substance. That is, when at least one of the monoclonal antibody of the present invention and an anti-HbA1c antibody is bound to latex particles which are insoluble carriers, and the latex particles are brought into contact with a specimen and an anti-Hb monoclonal antibody. The antibody-bound latex particles are crosslinked via the HbA0 or HbA1c in the sample, and agglutinations occur. Accordingly, from the changes in the intensity of agglutination, the relevant HbA0 or HbA1c can be specifically measured.

Alternatively, in the case of performing an assay by a competitive latex agglutination method, HbA0 or HbA1c can be measured by the following method, using purified HbA0 or HbA1c as a standard substance. That is, when at least one of the peptides VHLTPE (SEQ ID NO: 1) and f-VHLTPE (SEQ ID NO: 11) is bound to latex particles which are insoluble carriers, and the latex particles are brought into contact with a specimen and at least one of the monoclonal antibody of the present invention and an anti-HbA1c antibody, the HbA0 or HbA1c in the specimen shows a competitive inhibition in the agglutination reaction of the peptide-bound latex particles and the antibody. Therefore, the relevant HbA0 or HbA1c can be specifically measured from the change in the competitive inhibition.

There are no particular limitations on the specimen as long as it is a human body fluid containing HbA0 or HbA1c, and examples include blood and a red blood cell fraction.

There are no particular limitations on the latex particles that are used in the latex agglutination method or the like, as long as the particles serve as a carrier in the form of microparticles that is generally used in the immunological agglutination reactions and agglutination inhibition reactions utilizing a latex agglutination reaction. However, organic microparticles that can be industrially mass-produced are preferred. Examples of such organic microparticles include microparticles of a homopolymer or a copolymer of a vinyl-based monomer such as styrene, vinyl chloride, acrylonitrile, vinyl acetate, an acrylic acid ester, or a methacrylic acid ester; and a butadiene-based copolymer such as a styrene-butadiene copolymer or a methyl methacrylate-butadiene copolymer. Furthermore, reactive organic microparticles to which functional groups such as a carboxyl group, a primary amino group, a carbamoyl group, a hydroxyl group and an aldehyde group are bound, can also be used with preference. Among the latex particles described above, polystyrene-based latex particles of polystyrene, a styrene-butadiene copolymer or the like are preferred from the viewpoint that the the latex particles have excellent adsorbability of an antigen or an antibody and can stably maintain their biological activity for a long time.

There are no particular limitations on the shape of the latex particles. The average particle size is preferably a size sufficient for visually or optically detecting the agglutination product produced as a result of an agglutination reaction between the protein on the surface of the latex particles and the substance as an object of measurement. The average particle size is preferably 0.02 to 1.6 μm, and particularly preferably 0.03 to 0.5 μm.

There are no particular limitations on the method for binding the monoclonal antibody of the present invention or an anti-HbA1c antibody to latex particles, and any known method can be used. Examples include a method of physically adsorbing the antibody to the surface of latex particles, a method of covalently bonding the antibody to the surface of latex particles having a functional group, and a method of performing sensitization by immunological binding.

In the case of performing an assay by an immunochromatographic method, the method is particularly suitable because HbA0 and HbA1c can be simultaneously measured. For example, as shown in FIG. 1, use is made of an immunochromatographic support on which the monoclonal antibody of the present invention and an anti-HbA1c antibody are respectively immobilized at different sites (line A and line B). For the exposure treatment shown in FIG. 1, guanidine or a salt thereof and a nonionic surfactant; guanidine or a salt thereof and a nitrite; guanidine or a salt thereof, a nonionic surfactant and a nitrite; or conventionally known guanidine, thiocyanic acid, lithium thiocyanate, ferricyanide, an ionic surfactant, a nonionic surfactant, or the like can be used. A sample containing HbA0 and HbA1c whose epitopes are exposed, is added dropwise to a sample pad. The added sample flows with the capillary phenomenon. When the sample reaches the line A, only HbA0 in the sample reacts. When the sample reaches the line B, only HbA1c in the sample reacts. Other hemoglobins migrate to the end pad without reacting. When the density of color, reflection intensity, absorbance or the like of the line A and the line B is measured with an immunochromatographic reader, HbA0 and HbA1c in the sample can be respectively measured. Here, when the quantification value of HbA0 is designated as A, and the quantification value of HbA1c as B, HbA1c (%) can be determined by the formula: HbA1c (%)=(B/(A+B))×100.

Figure 2:
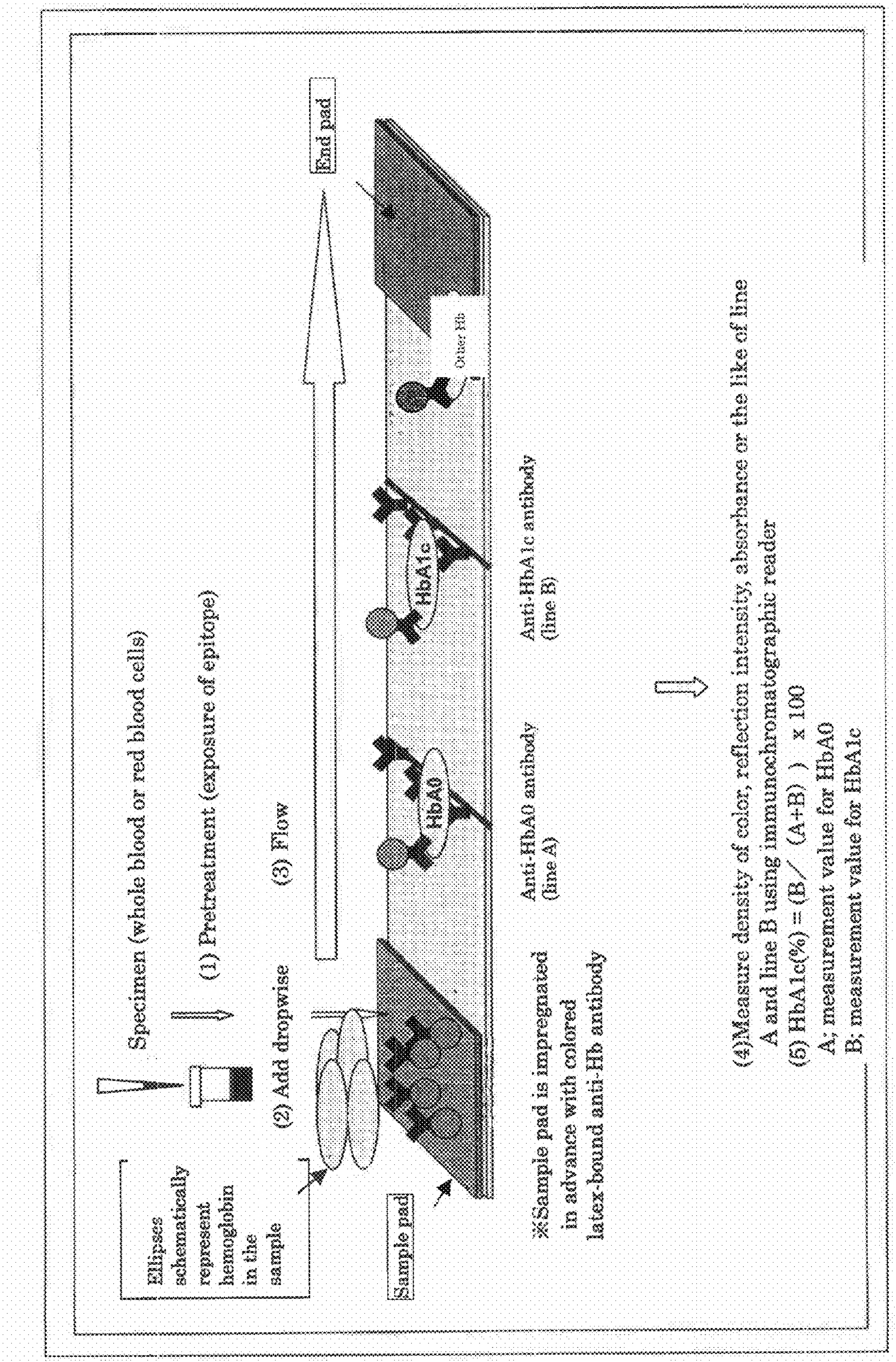
FIG. 2 is a schematic diagram showing the method for measuring HbA1c according to an immunochromatographic method.

Furthermore, in the immunochromatographic support, the sample pad is impregnated in advance with a colored latex-bound anti-Hb antibody (FIG. 2). The exposure treatment in FIG. 2 is carried out by the same treatment as described above. A sample containing HbA1c which has been exposed is added dropwise on the sample pad. The Hb (represented by an ellipse in FIG. 2) in the sample that has been added dropwise reacts with an anti-Hb antibody, and the reaction product migrates over the support. On the line A, a sandwich complex of anti-Hb antibody-HbA0-antibody of the present invention is formed. On the other hand, on the line B, a sandwich complex of anti-Hb antibody-HbA1c-anti-HbA1c antibody is formed. Other binding products of Hb and the anti-Hb antibody migrate to the end pad. When the amounts of the sandwich complexes thus formed are measured by measuring the density of color, reflection intensity, absorbance or the like of the line A and the line B using an immunochromatographic reader, the HbA0 and HbA1c in the sample can be respectively measured. Here, when the quantification value of HbA0 is designated as A, and the quantification value of HbA1c as B, HbA1c (%) can be determined by the formula: HbA1c (%)=(B/(A+B))×100.

In addition, gold colloidal particles and the like can also be used instead of the colored latex particles.

Here, the anti-HbA1c antibody may be a monoclonal antibody or a polyclonal antibody, and for example, those described in patent documents (Japanese Patent Application Laid-Open (JP-A) No. 61-172064, and JP-A No. 6-66796) can be used.

When the immunological assay methods described above are performed, a kit for immunological assay produced by using the antibody of the present invention and containing the antibodies, can be used. This kit may include general constituent elements that are used in an immunological assay method, for example, a labeling substance, a carrier, a support, a buffer solution, a stabilizer, and a reactor.

EXAMPLES

Next, the present invention will be specifically explained with examples, but these examples are not intended to limit the scope of the present invention.

Example 1

Production of Hybridoma and Acquisition of Antibody (I) Materials and Methods (1) Preparation of Purified HbA0 and Purified HbA1c A human red blood cell lysate was subjected to ion exchange chromatography using Bio-Rex70 (Bio-Rad Laboratories, Inc.), which is described in a non-patent document (Melisenda J. McDonald, et al., JBC, 253 (7), 2327-2332, 1978), to obtain purified HbA0 and HbA1c, and these were used in the subsequent experiments.

(2) Preparation of Various Peptides and Glycated Peptides

Peptides having various sequences were synthesized by Fmoc method using an automatic peptide synthesizer, and were purified. It was confirmed by HPLC that the purity of each of the peptides was 95% or higher. Furthermore, it was confirmed with a mass analyzer (MALDI-TOF) that the respective molecular weights of the peptides were identical with the theoretical values. Glycated peptides were synthesized and purified by the method described in the patent document (JP-A No. 61-172064). That is, peptides having various sequences and glucose were allowed to react in anhydrous pyridine, and the products were purified by HPLC. It was confirmed with a mass analyzer (MALDI-TOF) that the respective molecular weights of the glycated peptides were identical with the theoretical values, that is, the molecular weights obtained by adding 162 to the respective molecular weights of the peptides.

(3) Preparation of Anti-Hb Antibody and Anti-HbA1c Antibody

For the anti-Hb antibody, a mouse monoclonal antibody produced by a routine method using the purified HbA0 obtained in the above section (1) as an immunogen, was used. For the anti-HbA1c antibody, a mouse monoclonal antibody produced by a method described in a patent document (JP-A No. 61-172064) was used. That is, a glycated peptide (f-VHLTPEEKYYC) (SEQ ID NO: 9) synthesized in the above section (2) was bound to KLH, and this product was used as an immunogen. For the screening of hybridoma, a strain which reacts with purified HbA1c but does not react with purified HbA0 in antigen-immobilized ELISA, was selected.

(4) Preparation of Antigen for Immunization a. Peptides of various sequences in which cysteine was bonded to the C-terminal side of the N-terminal peptide of the β-chain of human hemoglobin (VHLC (SEQ ID NO: 3), VHLTC (SEQ ID NO: 4), VHLTPC (SEQ ID NO: 5), and VHLTPEC (SEQ ID NO: 6)) were prepared as described in the above section (2). These were respectively dissolved in 20 mmol/L phosphate buffer (pH 7.2; hereinafter, referred to as "PBS") containing 0.15 mol/L NaCl, to a concentration of 5 mg/mL.

b. Various commercially available (manufactured by Pierce Biotechnology, Inc.), maleimide-activated carrier proteins (OVA, BSA, cBSA and KLH) were respectively dissolved in purified water to a concentration of 5 mg/mL.

c. The peptide solution described above and the carrier protein solution were mixed in the ratio of 1:1, and then the mixtures were incubated for 2 hours at room temperature while moderately rotated.

d. Thereafter, the mixtures were dialyzed with PBS at 4° C. for 2 days.

e. The solutions obtained after the dialysis were collected and were each used as antigen for immunization.

(5) Immunization and Test Blood Collection

Each of the antigens for immunization was mixed with an adjuvant in the ratio of 1:1, and then the emulsion was prepared using a connection syringe. This emulsion was subcutaneously injected into the dorsal side of a female BALB/c mouse (20 to 50 μg per mouse). This operation (immunization) was repeated five times with a two-week interval between operations. Six weeks after the initiation of immunization, mouse antiserum was collected from the ocular fundus of each mouse, and the antibody titer in the antiserum was examined by the antigen-immobilized ELISA method that will be described below. Furthermore, in all of the ELISA methods, the serum collected from the ocular fundus of a non-immunized mouse was used as a control.

(6) Cell Fusion

Spleen was extracted from a mouse in which a high antibody titer was verified in the test blood collection described above, and cell fusion was carried out by a conventional method using 50% PEG1450 (manufacturedbySigma-AldrichCorpolation). SP2/O cells were used as the myeloma cells. The fused cells thus obtained were suspended in a RPMI1640 medium containing HAT and 15% bovine fetal serum such that the concentration of the spleen cells was $2.5\times10^6$ cells/mL, and the suspension was dispensed on a 96-well culture plate in an amount of 0.2 mL per well. These cells were cultured in a 5% $CO_2$ incubator at 37° C.

(7) Screening

Ten days after the cell fusion, the antigen-immobilized ELISA method that will be described later was carried out as the first screening assay using the culture supernatant, and wells showing high reactivity to purified HbA0 were selected as primary positive wells. The cells in the primary positive wells were subcultured on a 24-well plate.

Two days after the subculture, the competitive ELISA method that will be described later was carried out as the second screening assay using the culture supernatant, and wells showing high reactivity to the N-terminal peptide (VHLTPE) (SEQ ID NO: 1) of the β-chain of human hemoglobin and showing no reactivity to the glycated peptide of the same amino acid sequence (f-VHLTPE) (SEQ ID NO: 11), were selected as secondary positive wells.

(8) Cloning and Collection of Immunoglobulin (Antibody)

Five strains of hybridomas selected by the second screening were cloned by a limiting dilution method. Subsequently, in order to collect the immunoglobulin (antibody) produced by each hybridoma, the hybridoma was intraperitoneally administered in the number of $0.5\times10^6$ cells to a 12-week old female BALB/c mouse to which 0.5 mL of pristane had been intraperitoneally injected two weeks before. After 14 days, the ascites fluid was collected and centrifuged to obtain the supernatant. The supernatant was mixed with an equal volume of the adsorption buffer (3 mol/L NaCl, 1.5 mol/L Glycine-NaOH buffer solution, pH 8.5), and then the mixture was filtered. The filtrate was passed through a Protein A-Sepharose Column which had been equilibrated with the adsorption buffer, so as to adsorb the antibody in the filtrate to the column, and then elution was carried out with 0.1 mol/L citrate buffer (pH 3.0). The eluate was neutralized with a 1 mol/L Tris-HCl buffer (pH 8.0), and then dialysis was carried out with PBS to collect the antibody.

(9) Production of Plate for ELISA

Purified HbA0 which was prepared by dissolving in PBS to a concentration of 1 μg/mL was immobilized on a 96-well plate in an amount of 50 μL/well as an antigen for screening, and the plate was left to stand overnight at 4° C. The plate was washed three times with 400 μL/well of a 0.05% Tween 20-containing PBS (hereinafter, referred to as "PBST"), and then 100 μL/well of 1% BSA-containing PBST (hereinafter, referred to as "1% BSA-PBST") was dispensed. The plate was left to stand for one hour at room temperature and was subjected to blocking. Thus, the plate for ELISA was produced. The plate for ELISA was washed three times with PBST, and then various reagents were added to the plate so that the plate was used for the various ELISA tests described in the Examples.

(10) Antigen-Immobilized ELISA Method a. Each mouse antiserum or the culture supernatant of the fused cells, which had been diluted stepwise with 1% BSA-PBST, was dispensed on a plate for ELISA in an amount of 50 μL/well, and the plate was left to stand for one hour at room temperature.

b. The plate was washed three times with PEST, and then a solution prepared by diluting HRP-GtF $(ab')_2$-Anti-Mouse Ig's (manufactured by Biosource, Inc.) to 5000-fold with 1% BSA-PBST, was dispensed on the plate in an amount of 50 μL/well. The plate was left to stand for one hour at room temperature.

c. The plate was washed three times with PBST, and then a color developing solution in which ortho-phenylenediamine hydrochloride (ortho-phenylenediamine hydrochloride (manufactured by Tokyo Chemical Industry Co., Ltd.) and hydrogen peroxide were dissolved in a citrate buffer at pH 5.0 to concentrations of 2 mg/mL and 0.02%, respectively) (hereinafter, referred to as "OPD color developing solution"), was dispensed on the plate (50 μL/well). The plate was left to stand for 10 minutes at room temperature.

d. 0.75 mol/L sulfuric acid was dispensed on the plate in an amount of 50 μL/well to stop the reaction, and then the absorbance at 492 nm was measured with a plate reader.

(11) Competitive ELISA Method a. A solution prepared by diluting the N-terminal peptide (VHLTPE) (SEQ ID NO: 1) of the β-chain of human hemoglobin or the glycated peptide of the same amino acid sequence (f-VHLTPE) (SEQ ID NO: 11) with 1% BSA-PBST to an appropriate concentration, was dispensed on a plate for ELISA in an amount of 25 μL/well.

b. Subsequently, the culture supernatant of fused cells which had been diluted with 1% BSA-PBST to an appropriate concentration was dispensed on the plate in an amount of 25 μL/well, and the plate was left to stand for one hour at room temperature.

The subsequent operations were carried out in the same manner as in the steps b. to d. of the antigen-immobilized ELISA method described in the above section (10).

Figure 3:
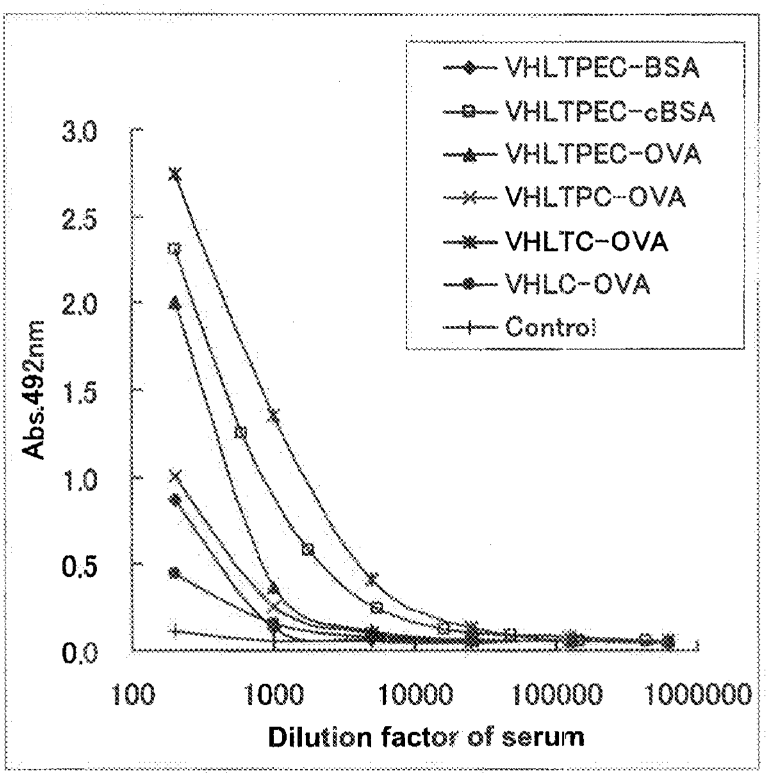
FIG. 3 shows the results obtained by measuring the antibody titers in mouse antisera by an antigen-immobilized ELISA method (FIG. 3 discloses SEQ ID NOS: 6, 6, 6, 5, 4, and 3, respectively, in order of appearance)

(II) Results (1) Results of Antigen-Immobilized ELISA Test in Test Blood Collection Test blood was collected, and the reactivity of the antibodies in various mouse antisera to purified HbA0 was investigated by an antigen-immobilized ELISA method. As a result, reactivity toward HbA0 was verified in all of the six kinds of mouse antisera (FIG. 3). It was considered that each of the mouse antisera obtained in the present example contained antibodies that specifically recognizes the N-terminal sequence of the Hb β-chain which is a common part in the complex of the N-terminal peptide of the β-chain of human hemoglobin and a carrier protein, which is an antigen for immunization, and HbA0 which is an antigen for screening.

(2) Screening

Cell strains which showed high reactivity to purified HbA0 that was immobilized in the first screening assay were selected, and the selected strains were further subjected to a second screening assay. As a result, it was found that five kinds of antibodies (85201, 85202, 85203, 85204 and 85206) showed high reactivity to the N-terminal peptide (VHLTPE) (SEQ ID NO: 1) of the β-chain of human hemoglobin, but did not show reactivity to the glycated peptide of the same amino acid sequence (f-VHLTPE) (SEQ ID NO: 11).

(3) Cloning and Collection of Immunoglobulin (Antibody)

The five kinds of antibodies selected by the second screening assay were subjected to cloning, and hybridomas producing the monoclonal antibodies were deposited with the International Patent Organism Depositary, National Institute of Advanced Industrial Science and Technology (dated Nov. 28, 2008; Tsukuba Central 6, 1-1-1 Higashi, Tsukuba, Ibaraki, Japan). The Accession Numbers are as follows.

Antibody No.: Accession No.

85201: FERM BP-11187

85202: FERM BP-11188

85203: FERM BP-11189

85204: FERM BP-11190

85206: FERM BP-11191

Example 2

Evaluation of Specificity of Monoclonal Antibodies Produced by Various Hybridomas (I) Materials and Methods (1) Preparation of Reagent The various antigens and antibodies used in the evaluation were prepared by operations similar to those used in the sections (1) to (4) of Example 1. For the HPLC fractions, human red blood cell lysate was separated by KO500 method using a TSK-gel GlycoHSi column manufactured by Tosoh Corp., and the fractions collected using a fraction collector were used. When the fractions were to be added to antigen-immobilized ELISA, each of the fractions was used after diluting to 6-fold with PBS.

(2) Evaluation of Specificity

The evaluation was carried out in the same manner as in the antigen-immobilized ELISA and competitive ELISA methods of Example 1. However, the antibody used therein was purified IgG (monoclonal antibody: 0.2 μg/mL).

(II) Results (1) Reactivity to Peptide and Glycated Peptide

Figure 4:
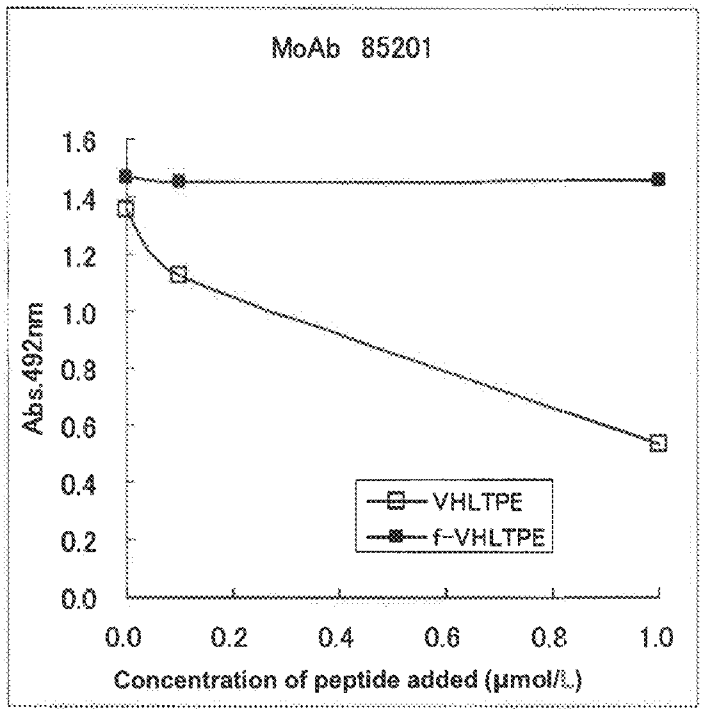
FIG. 4 shows the results obtained by examining the reactivity of the antibody of the present invention to the N-terminal peptide (VHLTPE) (SEQ ID NO: 1) of the hemoglobin β-chain and the glycated peptide (f-VHLTPE) (SEQ ID NO: 11) by a competitive ELISA method.
Figure 4:
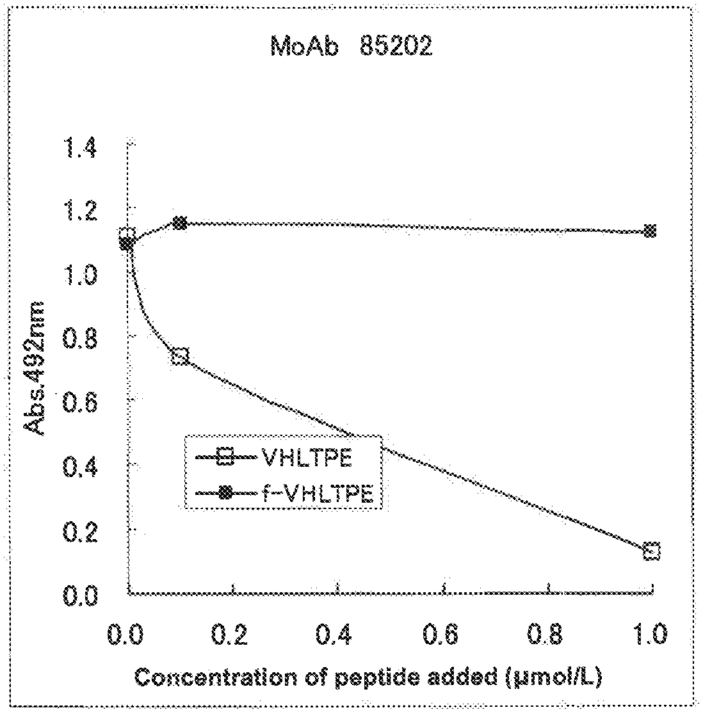
Figure 5:
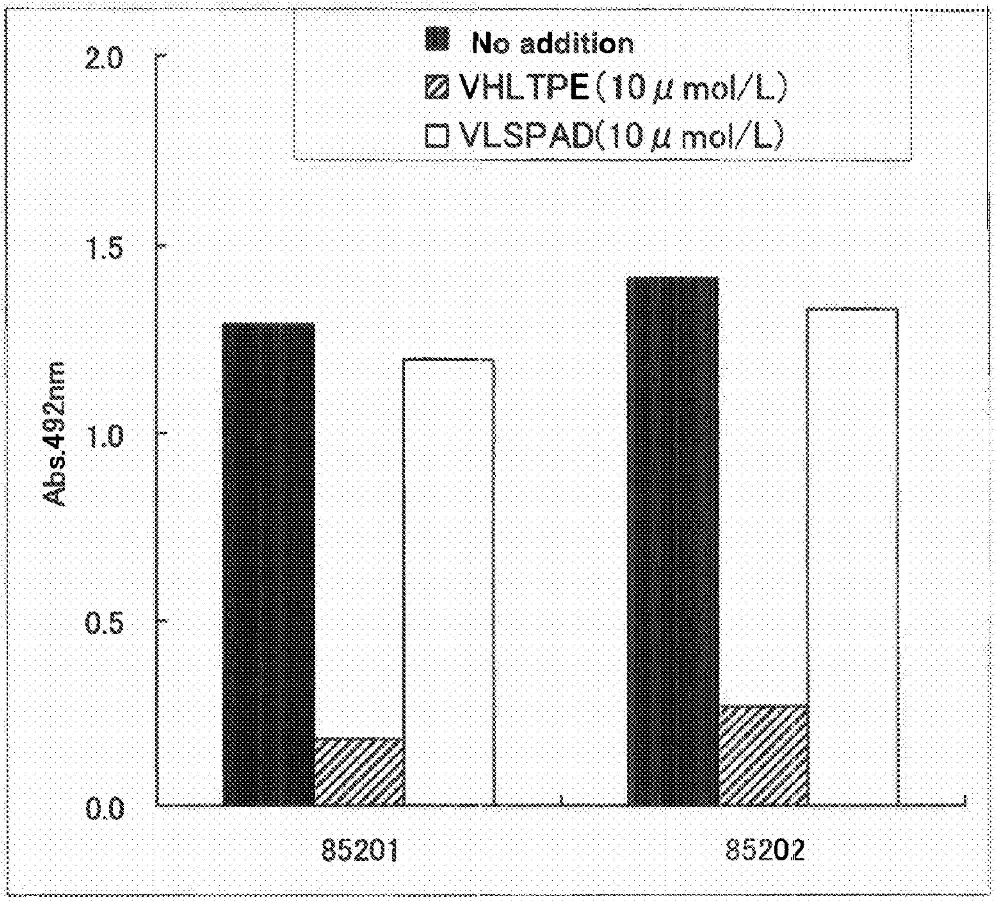
FIG. 5 shows the results obtained by examining the reactivity of the antibody of the present invention to the N-terminal peptide of the hemoglobin β-chain (VHLTPE) (SEQ ID NO: 1) and the N-terminal peptide of the α-chain (VLSPAD) (SEQ ID NO: 10) by a competitive ELISA method.

First, as shown in FIG. 4, it was confirmed that specific antibodies (85201 and 85202) used in the test for competitive ELISA, both reacted only with the N-terminal peptide (VHLTPE) (SEQ ID NO: 1) of the n-chain of human hemoglobin but did not react with the glycated peptide of the same amino acid sequence (f-VHLTPE) (SEQ ID NO: 11). Furthermore, as shown in FIG. 5, it was confirmed that the antibodies did not react with the N-terminal peptide (VLSPAD) (SEQ ID NO: 10) of the α-chain of human hemoglobin. The other three kinds of specific antibodies (85203, 85204 and 85206) were also subjected to the same test, and as a result, it was confirmed that the antibodies reacted only with the peptide VHLTPE (SEQ ID NO: 1) but did not react with f-VHLTPE (SEQ ID NO: 11) and VLSPAD (SEQ ID NO: 10).

(2) Reactivity to Purified HbA0 and Purified HbA1c

Figure 6:
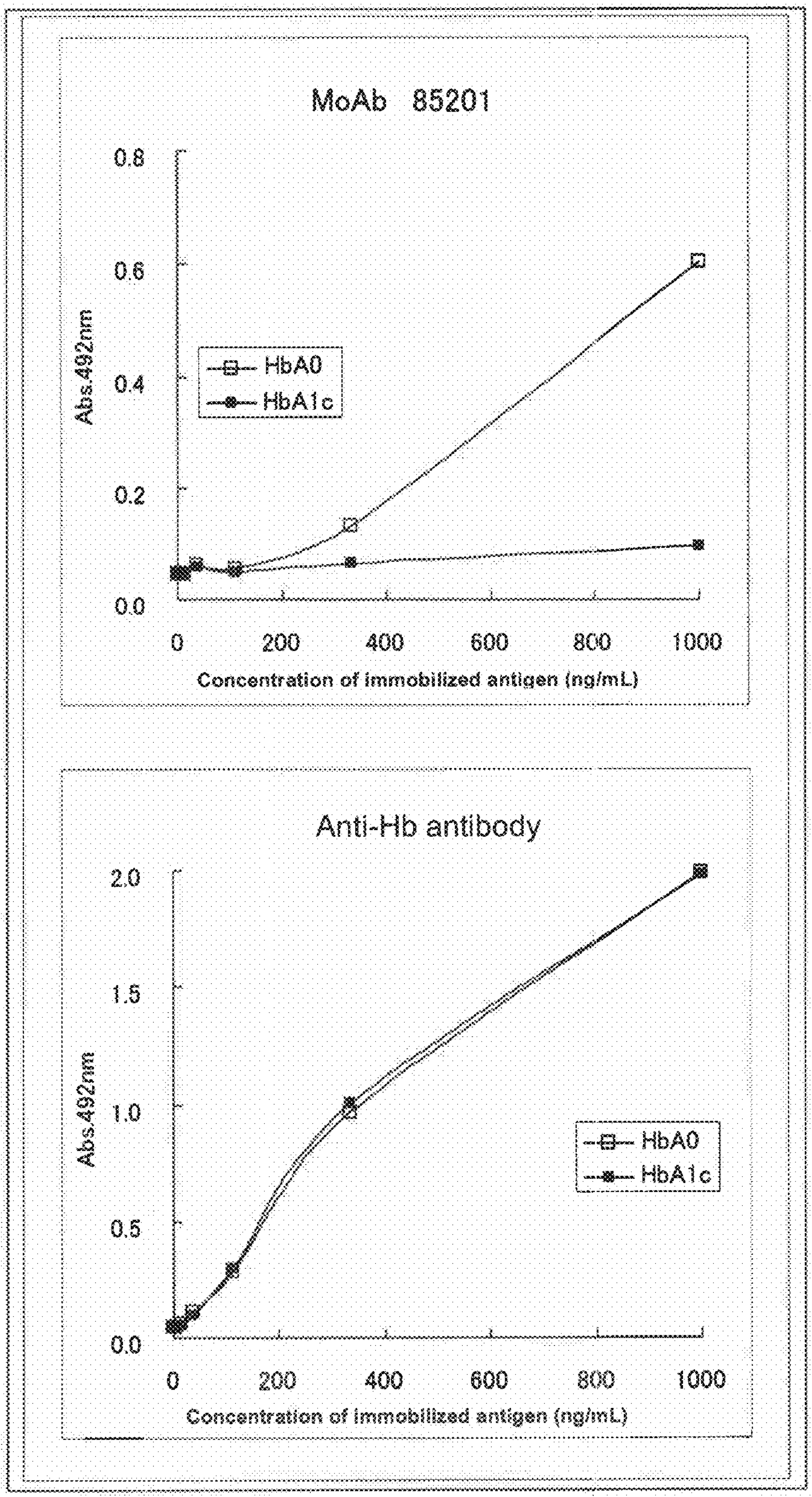
FIG. 6 shows the results obtained by examining the reactivity of the antibody of the present invention and an anti-hemoglobin antibody to HbA1c and HbA0 by an antigen-immobilized ELISA method.

As shown in FIG. 6, first, the anti-Hb antibody that was used as a control in antigen-immobilized ELISA reacted equally with purified HbA0 and purified HbA1c. On the contrary, a specific antibody used in the test (85201) did not react with HbA1c but reacted only with HbA0. The other four specific antibodies (85202, 85203, 85204 and 85206) were subjected to the same test, and as a result, it was confirmed that the antibodies reacted only with purified HbA0 but did not react with purified HbA1c.

(3) Reactivity to HPLC Fraction

Figure 7:
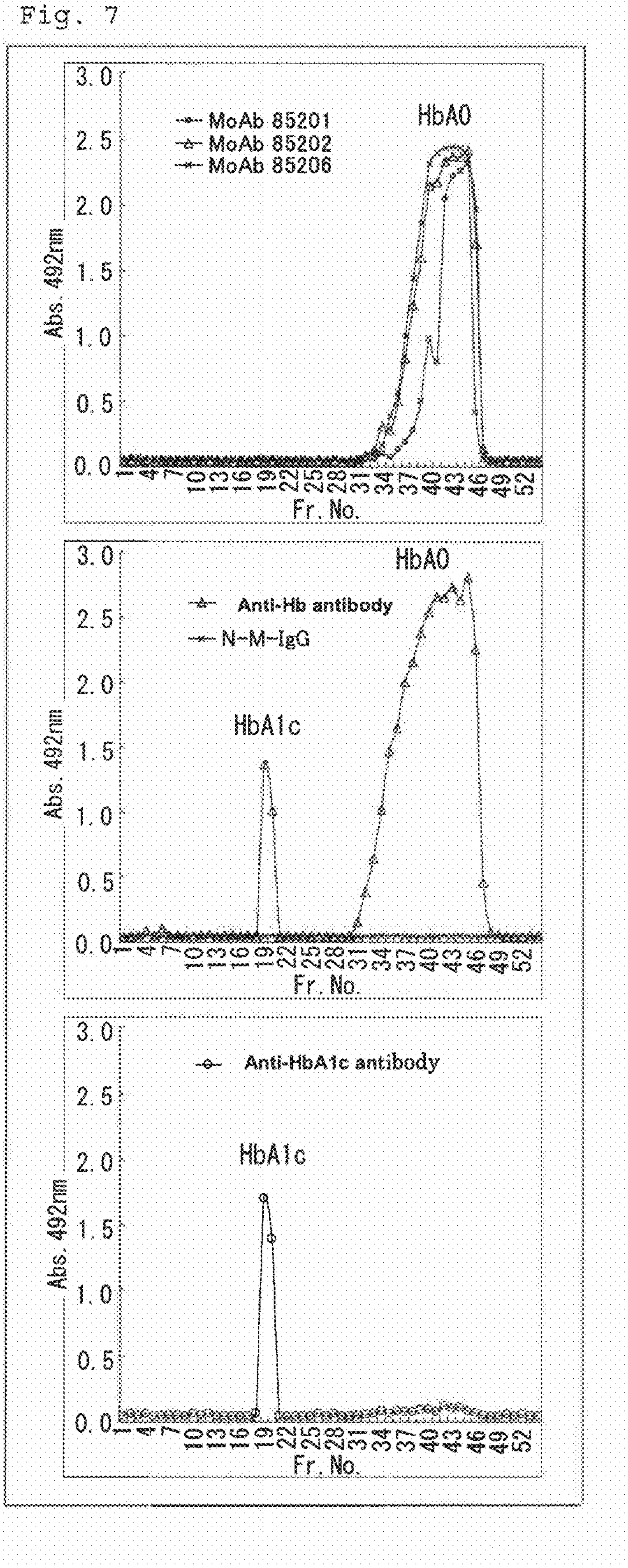
FIG. 7 shows the results obtained by examining the reactivity of the antibody of the present invention, an anti-hemoglobin antibody, and an anti-HbA1c antibody to hemoglobin subfractions separated by HPLC, by an antigen-immobilized ELISA method.

As shown in FIG. 7, first, the anti-Hb antibody that was used as a control in antigen-immobilized ELISA reacted with both HbA1c and HbA0, and the anti-HbA1c antibody that was similarly used as a reference reacted only with the peak of HbA1c but did not react with the peak of HbA0. On the contrary to this, three kinds of specific antibodies that were used in the test (85201, 85202 and 85206) did not react with HbA1c but reacted only with HbA0. The other two kinds of specific antibodies (85203 and 85204) were also subjected to the same test, and as a result, it was confirmed that the antibodies reacted with HbA0 but did not react with HbA1c.

From the above results, it was confirmed that the five kinds of specific antibodies that were used in the test do not react with HbA1c but react only with HbA0, and that these antibodies are capable of detecting the N-terminal hexapeptide sequence (VHLTPE) (SEQ ID NO: 1) of hemoglobin β-chain.

Example 3

Measurement of HbA1c Value by ELISA (I) Materials and Methods (1) Preparation of Anti-HbA1c Antibody and Anti-Hb Antibody The anti-HbA1c antibody and anti-Hb antibody used in the assay were prepared in the same manner as in section (I) (3) of Example 1.

(2) Preparation of Biotin-Labeled Anti-Hb Antibody

The anti-Hb antibody of the above section (1) was labeled as follows, using a commercially available biotin labeling reagent (Pierce Biotechnology, Inc.; EZ-Link Sulfo-NHS-LC-Biotin). 0.05 mL of the biotin labeling reagent which had been dissolved in PBS to a concentration of 10 mg/mL, was added to 1 mL of an anti-Hb antibody solution at a concentration of 1 mg/mL, and the mixture was allowed to react for 2 hours at room temperature. After the reaction, the antibody was dialyzed with PBS and then was used in the assay.

(3) Preparation of Specimen and Standard Sample

Blood was collected from employee volunteers using EDTA-2Na-containing vacuum blood collection tubes (manufactured by Sekisui Medical Co., Ltd.), and red blood cells were separated by centrifugation. Four μL of these red blood cells were mixed with 0.2 mL of an antigen treatment solution (1% Tween 20-10 mmol/L $NaNO_2$-3 mol/L guanidine hydrochloride-5 mmol/L MES, pH 6.0). The mixture was left to stand for 10 minutes at 25° C., and then the mixed solution was diluted stepwise with 3% skimmed milk-PBST. This dilution was used as a specimen for sandwich ELISA as follows. Furthermore, for a standard sample, a specimen of another person, of which the HbA1c concentration and the HbA0 concentration had been previously determined by a HPLC method as described below, was used.

(4) Measurement of Amount (Concentration) of HbA0 by Sandwich ELISA a. A specific antibody obtained in Example 1 (85201) was diluted with PBS to a concentration of 5 μg/mL. This dilution was dispensed on an ELISA plate in an amount of 50 μL/well, and the plate was left to stand overnight at 4° C.

b. The plate was washed three times with PBST (350 μL/well), and then 1% BSA-PBST was dispensed on the plate in an amount of 100 μL/well. The plate was left to stand for one hour at room temperature.

c. The plate was washed three times with PBST, and then the standard sample or specimen which had been treated in the above section (3) was dispensed on the plate in an amount of 50 μL/well. The plate was left to stand for one hour at room temperature.

d. The plate was washed three times with PBST, and then the biotin-labeled anti-Hb antibody which was diluted with 1% BSA-PBST to a concentration of 1 μg/mL was dispensed on the plate in an amount of 50 μL/well. The plate was left to stand for one hour at room temperature.

e. The plate was washed three times with PBST, and then HRP-Streptavidin (manufactured by Pierce Biotechnology, Inc.) diluted with 1% BSA-PBST to a concentration of 1 μg/mL was dispensed on the plate in an amount of 50 μL/well. The plate was left to stand for 30 minutes at room temperature.

f. The plate was washed three times with PBST, and then the OPD color developing solution was dispensed on the plate (50 μL/well). The plate was left to stand for 10 minutes at room temperature.

g. 0.75 mol/L sulfuric acid was dispensed on the plate in an amount of 50 μL/well to stop the reaction, and then the absorbance at 492 nm was measured with a plate reader.

h. A calibration curve was produced based on the absorbance of the standard sample at various concentrations, and the concentration of the specimen was determined using the calibration curve.

(5) Measurement of Amount (Concentration) of HbA1c by Sandwich ELISA

The HbA1c concentration was measured by the same method as that used in the above section (4), using an anti-HbA1c antibody instead of the specific antibody (85201).

(6) Calculation of HbA1c Value

The HbA1c value (content of HbA1c) was determined by the following formula, based on the HbA0 concentration and HbA1c concentration determined in the above sections (4) and (5).

HbA1c content (%)=(Amount (concentration) of HbA1c/(amount (concentration) of HbA1c+ amount (concentration) of HbA0))×100

(7) Measurement of HbA1c Value According to HPLC Method

The content of HbA1c in the total amount of hemoglobin was measured using a Tosoh automatic glycohemoglobin analyzer, HLC-723G8.

(II) Results (1) Calibration Curve

Figure 8:
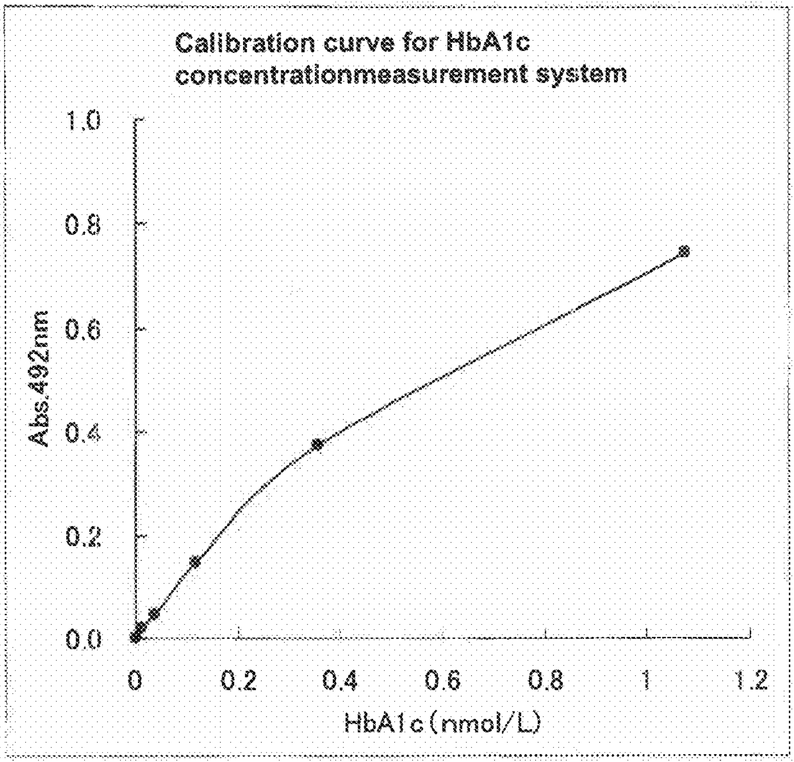
FIG. 8 shows calibration curves for a HbA1c concentration measurement system and a HbA0 concentration measurement system based on sandwich ELISA.
Figure 8:
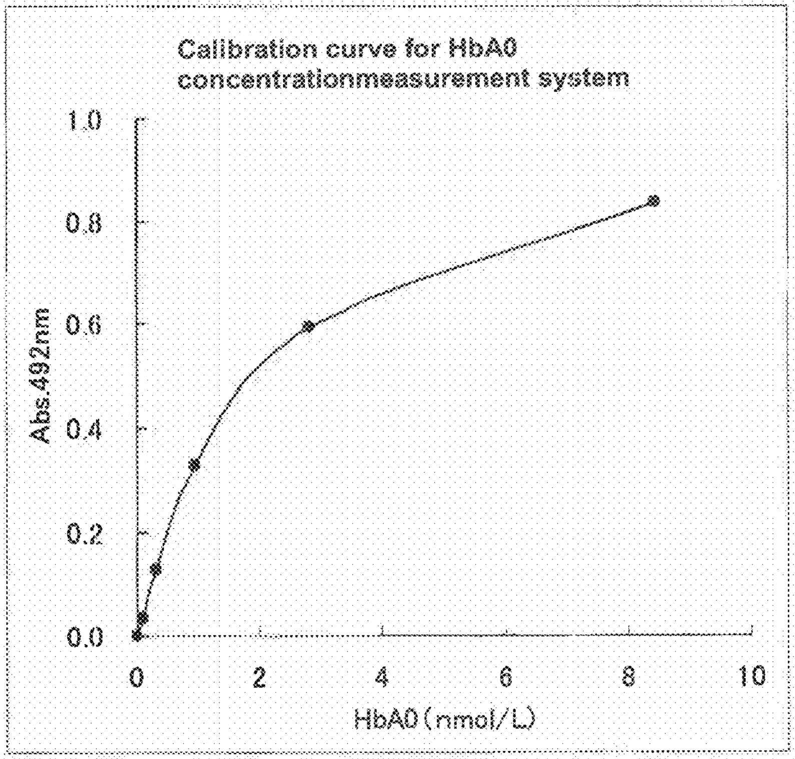

Calibration curves for a HbA0 concentration measurement system and a HbA1c concentration measurement system were produced by using standard samples. As shown in FIG. 8, an antigen concentration-dependent increase in the absorbance was confirmed in both of the measurement systems.

(2) Comparison with Measurement Values According to HPLC Method

The HbA1c values determined by sandwich ELISA, as described above, using the antibody of the present invention, were compared with the HbA1c values determined by the HPLC method. Specimens collected from five normal adults were used, and the HbA1c values were determined respectively by the two methods. As a result, as shown in Table 1, the HbA1c values determined by the two methods were approximately the same.

TABLE 1

| | HbAlc (%) | |
|---|---|---|
| No. | Tosoh HPLC | Sandwich ELISA |
| 1 | 5.2 | 5.3 |
| 2 | 5.2 | 4.5 |
| 3 | 4.8 | 4.4 |
| 4 | 4.8 | 5.2 |
| 5 | 5.0 | 5.5 |

From the results shown above, it was confirmed that the antibody of the present invention can be used in quantitative measurement of the amount (concentration) of HbA0, the amount (concentration) of HbA1c, and the HbA1c value (content of HbA1c).

The invention claimed is:

1. An antibody which specifically binds with a peptide or a protein comprising the amino acid sequence of VHLTPE (SEQ ID NO: 1) at the N-terminus in which the N-terminal valine is not modified, but does not specifically bind with a peptide or a protein comprising the amino acid sequence of VHLTPE (SEQ ID NO: 1) at the N-terminus in which the N-terminal valine is modified with a sugar, wherein the antibody is produced by a hybridoma selected from the group consisting of 85201, deposited as FERM BP-11187, 85202, deposited as FERM BP-11188, 85203, deposited as FERM BP-11189, 85204, deposited as, and 85206, deposited as FERM BP-11191.

2. The antibody of claim 1, which is produced by the hybridoma 85201 (FERM BP-11187).

3. The antibody of claim 1, which is produced by the hybridoma 85202 (FERM BP-11188).

4. The antibody of claim 1, which is produced by the hybridoma 85203 (FERM BP-11189).

5. The antibody of claim 1, which is produced by the hybridoma 85204 (FERM BP-11190).

6. The antibody of claim 1, which is produced by the hybridoma 85206 (FERM BP-11191).

7. A method of producing an antibody, the method comprising culturing one or more hybridomas selected from the group consisting of 85201, deposited as FERM BP-11187, 85202, deposited as FERM BP-11188, 85203, deposited as FERM BP-11189, 85204, deposited as FERM BP-11190, and 85206, deposited as FERM BP-11191, to produce the antibody from the one or more hybridomas.

8. The method of claim 7, comprising culturing of the hybridoma 85201 (FERM BP-11187).

9. The method of claim 7, comprising culturing the hybridoma 85202 (FERM BP-11188).

10. The method of claim 7, comprising culturing the hybridoma 85203 (FERM BP-11189.

11. The method of claim 7, comprising culturing the hybridoma 85204 (FERM BP-11190).

12. The method of claim 7, comprising culturing the hybridoma 85206 (FERM BP-11191).

* * * * *

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val His Leu Thr Pro Glu
1               5


<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 2

Val His Leu
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Val His Leu Cys
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Val His Leu Thr Cys
1 5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Val His Leu Thr Pro Cys
1 5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Val His Leu Thr Pro Glu Cys
1 5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Val His Leu Thr
1

<210> SEQ ID NO 8
<211> LENGTH: 5
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 8

Val His Leu Thr Pro
1               5


<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val His Leu Thr Pro Glu Glu Lys Tyr Tyr Cys
1               5                   10


<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Leu Ser Pro Ala Asp
1               5


<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term glycated

<400> SEQUENCE: 11

Val His Leu Thr Pro Glu
1               5
```